United States Patent [19]

McFarlan

[11] Patent Number: 5,659,077
[45] Date of Patent: Aug. 19, 1997

[54] PRODUCTION OF ACETIC ACID FROM METHANE

[75] Inventor: Andrew J. McFarlan, Stittsville, Canada

[73] Assignee: Natural Resources Canada, Ottawa, Canada

[21] Appl. No.: 620,659

[22] Filed: Mar. 22, 1996

[51] Int. Cl.$^6$ .................................................. C07C 27/10
[52] U.S. Cl. ................. 562/512.2; 518/701; 568/910.5
[58] Field of Search ................. 562/512.2; 568/910.5; 518/701

[56] References Cited

U.S. PATENT DOCUMENTS

| | | | |
|---|---|---|---|
| 4,250,346 | 2/1981 | Young et al. | 585/658 |
| 4,982,023 | 1/1991 | Han et al. | 568/910.5 |
| 5,162,578 | 11/1992 | McCain, Jr. et al. | 562/512.2 |
| 5,278,319 | 1/1994 | Ramachandran et al. | 549/249 |

FOREIGN PATENT DOCUMENTS

| | | | |
|---|---|---|---|
| 0526974 | 6/1992 | European Pat. Off. | 51/12 |
| 0526974A1 | 6/1992 | European Pat. Off. | 51/12 |

OTHER PUBLICATIONS

Howard et al.; Catalysis Today, 18 pp. 325-354 (1993).

Primary Examiner—C. Warren Ivy
Assistant Examiner—Sreeni Padmanabhan

[57] ABSTRACT

The novel integrated process for production of acetic acid comprises the steps of subjecting a feed mixture consisting of (a) methane gas and (b) gaseous oxygen, air, or a mixture thereof to partial oxidation without production of synthesis gas in a reaction zone at elevated temperature and pressure to form a reaction mixture containing methanol, carbon monoxide, carbon dioxide, methane and water vapor. At least a portion of the water vapor is removed from the reaction mixture, and the remaining partial oxidation reaction mixture is fed, together with additional methanol from an external source, through a carbonylation reaction zone at elevated temperature and pressure to form a reaction product containing acetic acid and/or methyl acetate and methanol. The additional methanol is added in an amount such that the additional methanol together with the methanol produced by partial oxidation is sufficient to convert substantially all of the carbon monoxide produced by partial oxidation. Excess methane and carbon dioxide are recycled from the carbonylation reaction zone back to the partial oxidation reaction zone, and methanol in the carbonylation reaction product is recycled back to the carbonylation reaction zone and acetic acid and/or methyl acetate is recovered as product.

14 Claims, 1 Drawing Sheet

PRODUCTION OF ACETIC ACID FROM METHANE

FIELD OF THE INVENTION

The present invention is directed to an integrated process for converting methane to acetic acid, in which methane (natural gas) is converted to methanol and carbon monoxide by a direct partial oxidation and, in the same process stream, methanol and carbon monoxide are converted to acetic acid via methanol carbonylation.

BACKGROUND OF THE INVENTION

The catalyzed carbonylation reaction of methanol with carbon monoxide provides an important synthetic route to acetic acid, and is significant as a $C_1$ conversion process for producing bulk chemicals. As the third largest end use of synthetic methanol, acetic acid production consumes large quantities of methanol and carbon monoxide, one or both of which may be obtained from synthesis gas.

Methanol is the largest volume commodity chemical derived from $C_1$ conversion processes, with 1993 production exceeding 2.1 million tonnes in Canada and 4.8 million tonnes in the U.S.A. Methanol serves as a building block for synthesizing many important chemicals. The largest end uses of synthetic methanol are the manufacture of methyl tertiary butyl ether (MTBE) via a catalytic addition reaction with isobutylene and the manufacture of formaldehyde via catalytic oxidation of methanol. The manufacture of acetic acid is the third largest end use of synthetic methanol and world production capacity for acetic acid is estimated at about 5.6 million tonnes annually, and about 60% of this capacity is based on the catalytic carbonylation reaction of methanol with carbon monoxide. In 1993, U.S. production of acetic acid exceeded 1.7 million tonnes. As such, the catalysed carbonylation reaction of methanol provides an important synthetic route to acetic acid and is significant as a $C_1$ conversion process for producing bulk chemicals. Thus, it will be recognized that the economics of commercial acetic acid production are closely linked to those of methanol production.

There are a variety of commercial processes for producing acetic acid by methanol carbonylation. A common process begins with synthesis gas production and includes the steps of: synthesis gas production, synthesis gas to methanol conversion, carbon monoxide/hydrogen separation from synthesis gas, methanol carbonylation and acetic acid recovery.

Although the syngas route to acetic acid is currently an economically attractive process for large scale acetic acid production, several energy intensive intermediate steps add to the overall production costs. For instance, there is the cost of synthesis gas production, both in energy consumed and capital investment required. There is a further cost in hydrogen/carbon monoxide separation, which is again capital intensive and inefficient if there is no immediate use for the hydrogen other than its fuel value. Finally, there is capital and operating costs associated with decompression and compression of the process streams for the various synthesis steps.

Various researchers have described processes for, oxidation of methane to methanol. For instance, Hah et al. in U.S. Pat. No. 4,982,023 describe a process for the synthesis of methanol by the homogeneous direct partial oxidation of natural gas or other source of methane using a reactor in which the reactor space is filled with inert, refractory inorganic particles. Ramachandran et al., U.S. Pat. No. 5,278,319 describes a process for the production of hydrocarbon partial oxidation products in which the concentration of carbon monoxide and all parts of the system is maintained at a high level.

There is also much published information on the production of acetic acid from methanol. For instance European Patent Publication No. 0 526 974 A1, published Feb. 10, 1993 describes a process for preparing acetic acid which comprises contacting methanol with the carbon monoxide or a mixture of carbon monoxide with hydrogen of 2% by volume or less in the presence of a carbon-supported rhodium metal catalyst and methyl iodide promoter in vapor phase. In *Catalysis Today* 18 (1993) 325–354, Howard et al., have provided a far reaching discussion relating to the carbonylation of methanol to acetic acid, including a lengthy discussion of the catalysis that may be used in this reaction.

There remains a need for a simplified and less expensive route for converting methane to acetic acid which can avoid many of the expensive intermediate steps presently used.

SUMMARY OF THE INVENTION

The present invention relates to an integrated process which in a unique way has succeeded in integrating the two basic process reactions of producing methanol and carbon monoxide via methane partial oxidation and the production of acetic acid via carbonylation reaction of methanol with carbon monoxide, resulting in a direct process of converting methane to acetic acid. The novel integrated process comprises the steps of subjecting a feed mixture consisting of (a) methane gas and (b) gaseous oxygen, air, or a mixture thereof to partial oxidation in a reaction zone at elevated temperature and pressure to form a reaction mixture containing methanol, carbon monoxide, carbon dioxide, methane and water vapor. At least a portion of the water vapor is removed from the reaction mixture, and the remaining partial oxidation reaction mixture is fed, together with additional methanol from an external source, through a carbonylation reaction zone at elevated temperature and pressure to form a reaction product containing acetic acid and/or methyl acetate and methanol. The additional methanol is added in an amount such that the additional methanol together with the methanol produced by partial oxidation is sufficient to convert substantially all of the carbon monoxide produced by partial oxidation. Excess methane and carbon dioxide are recycled from the carbonylation reaction zone back to the partial oxidation reaction zone, and methanol in the carbonylation reaction product is recycled back to the carbonylation reaction zone and acetic acid and/or methyl acetate is recovered as product.

The above process is both novel and advantageous because:

1. The process converts methane to acetic acid without the intermediate synthesis gas production, methanol synthesis and $CO/H_2$ separation.
2. The integration of the two processes results in a higher carbon efficiency and higher single pass yields without gas separation compared to methanol production via direct partial oxidation of methane. This is because methanol and carbon monoxide are consumed in the same process stream in the carbonylation reactor. The single pass yield of acetic acid can be significantly higher than the best methanol yields obtained by partial oxidation reaction at the same methane conversion.
3. There is value-added advantage due to the price differential between acetic acid and methanol.
4. The process pressure for the partial oxidation reaction of methane and the carbonylation reaction of methanol are roughly the same. Thus, decompression and compression of the process stream is minimized, resulting in lower capital and operating costs.

There are a number of important features to the process of the present invention beyond simply integrating two processes. Thus, it is the primary object of the present invention to be able to integrate the two processes in a simple manner. This means that the carbonylation reaction must be able to accept the reaction products from the partial oxidation reaction without substantial modification. One of the products of partial oxidation is carbon dioxide and this can be fed to the carbonylation reaction zone in quantities of typically up to about 20% by volume, preferably 4–10% by volume, of the reaction mixture. In the process of the invention, the carbon dioxide is recycled with excess methane from the carbonylation reaction zone back to the partial oxidation reaction zone. In order to control the level of carbon dioxide in the recirculating stream at an acceptable amount, a portion of the carbon dioxide may be removed from the reaction product of the partial oxidation stage by passing the reaction product stream through a scrubber to remove a portion of the carbon dioxide. The carbon dioxide dilutes the methane stream in the partial oxidation zone and also facilitates carbon dioxide scrubbing from the recycle stream at higher partial pressure.

It is also important that the feed stream to the carbonylation reaction zone have a low level of hydrogen, preferably less than 2% by volume. It has been found according to the present invention that the hydrogen can be maintained at an acceptable low level by operating the partial oxidation reaction at a pressure of at least 750 psi, preferably 1000–1500 psi.

Another important feature of the present invention is that the carbon monoxide produced by partial oxidation of methane is all used directly for the production of acetic acid. In order to make full use of the carbon monoxide produced, it is necessary according to the invention to feed to the carbonylation reaction zone an additional methanol stream from an external source. Thus, part of the methanol in the feed stream to the methanol carbonylation reaction zone is the methanol produced by the partial oxidation and the balance of the methanol in the feed stream required to convert all of the carbon monoxide in the stream to acetic acid is methanol obtained from an external source. This methanol from an external source is usually less than 50% by weight of the total methanol in the feed stream to the carbonylation reaction zone.

The product yield of methanol and carbon monoxide is not adversely affected when up to about 10% by volume of carbon monoxide is present in the feed stream to the partial oxidation zone. It is also advantageous to carry excess carbon monoxide in the system to raise the partial pressure in the carbonylation reaction zone. Thus, it has been found that in the integrated process of this invention it is advantageous to maintain the concentration of carbon monoxide in the process stream in the range of about 2–20% by volume, preferably about 5–10% by volume.

The partial oxidation reactor is preferably operated at a temperature in the range of 300° to 500° C., while the carbonylation reactor is preferably operated at a temperature in the range of 150° to 300° C. It is also preferable to conduct the carbonylation under heterogeneous catalysis. A variety of catalysts may be used, such as rhodium, iridium, cobalt, nickel, etc. The catalyst may be promoted by an iodide, e.g. methyl iodide.

DESCRIPTION OF THE PREFERRED EMBODIMENTS

Figure 1:
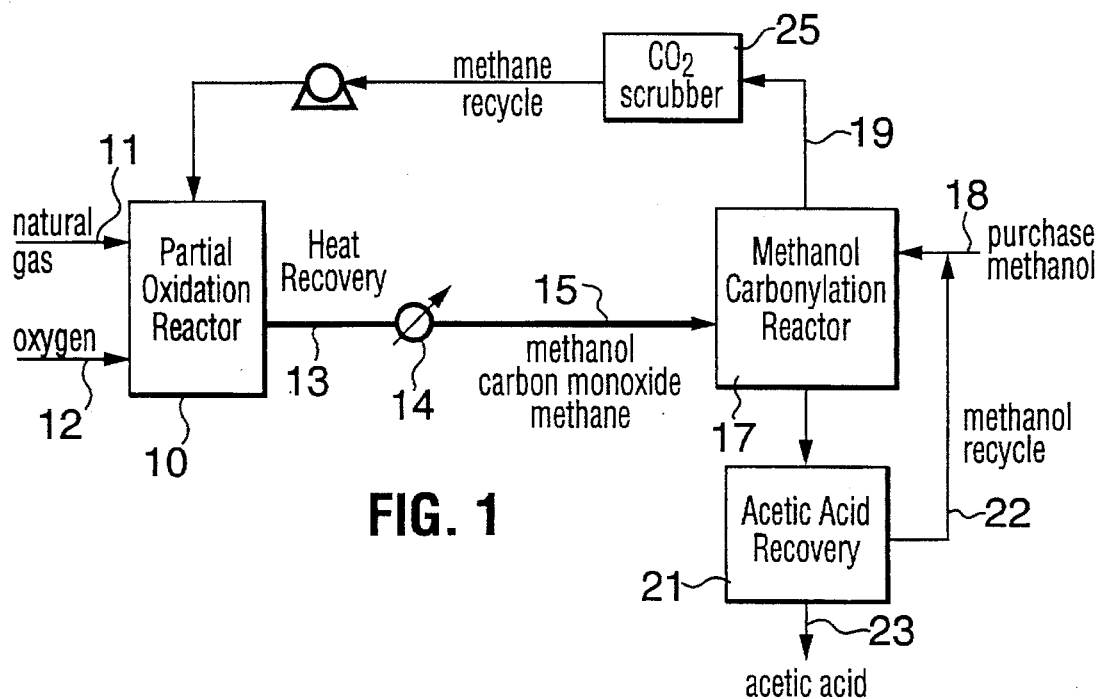
FIG. 1 illustrates, in block diagram, one embodiment of a system producing acetic acid according to the invention.

As shown in FIG. 1, the process of the present invention utilizes a partial oxidation reactor 10 to which is fed a natural gas stream 11 and an oxygen stream 12. The reaction product 13 is passed through a waste heat boiler 14 to recover excess heat of reaction. If necessary, some water may be removed from the reaction product. The product stream 15 then continues to the carbonylation reactor 17 where the carbonylation of methanol and carbon monoxide takes place in the presence of a catalyst. Additional methanol from an external source is fed into the reactor via inlet line 18. Excess methane and carbon dioxide are recycled to the partial oxidation reactor 10 via recycle line 19. This recycle stream passes through a scrubber 25 for removing carbon dioxide so that the concentration of carbon dioxide in the flow system of the invention is controlled within an acceptable level.

The reaction product from the carbonylation reactor 20 is fed to an acetic acid recovery system 21. Methanol present in the recovery system is recycled via line 22 to the carbonylation reactor 17 and product acetic acid 23 is recovered from the recovery system 21.

Figure 2:
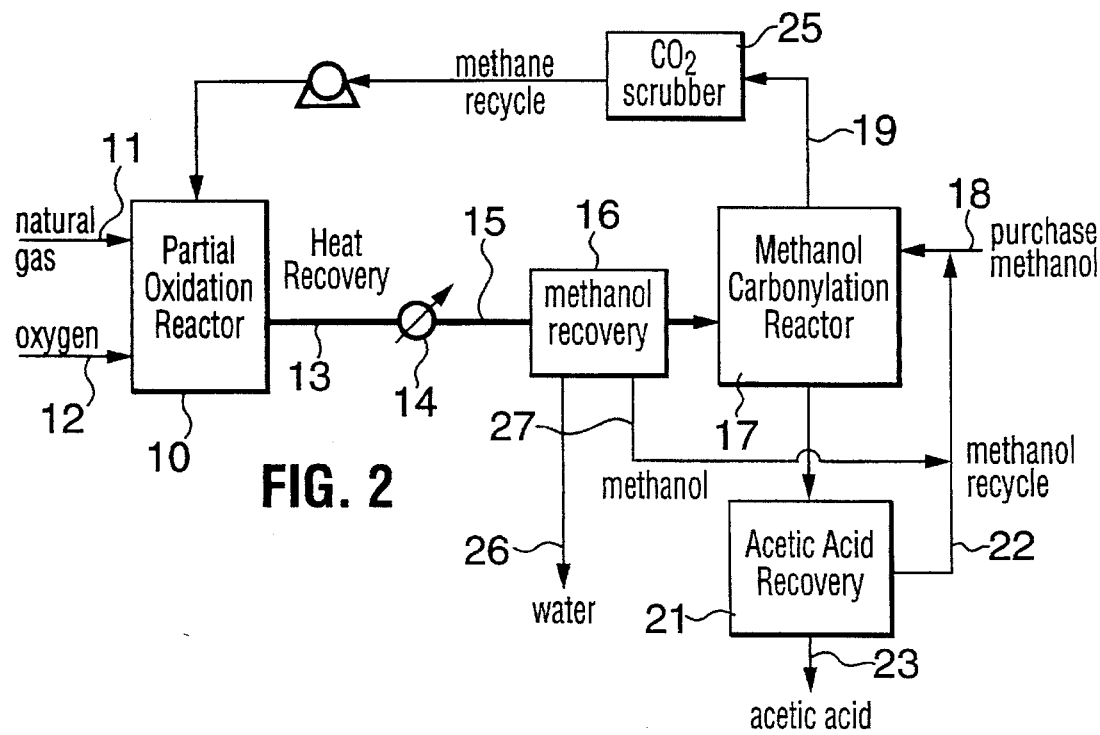
FIG. 2 illustrates, in block diagram, an alternative embodiment of the system illustrated in FIG. 1.

FIG. 2 shows an alternative embodiment of the invention. It is similar to the process of FIG. 1, but includes a water and methanol separator 16 for separating water and methanol from product stream 15. Water is recovered via line 26 and the methanol is fed to the carbonylation reactor via line 27.

Certain preferred features of the present invention are illustrated by the following non-limiting Examples.

EXAMPLE 1

A laboratory scale test was carried out in which the partial oxidation reactor was operated at a pressure of 1000 psig, a temperature of 425° C. and a GHSV of 4000/h. The fixed bed reactor having an internal diameter of 6.35 mm was packed with about 1.5 mL quartz chips. Under these conditions, 6% methane is converted per pass and oxygen reacts substantially completely. The reactants used and the results obtained are summarized in Table 1 below:

TABLE 1

|  | Inlet | | Outlet | |
| --- | --- | --- | --- | --- |
|  | mmol/h | mg/h | mmol/h | mg/h |
| methane | 187.6 | 3009 | 175.9 | 2822 |
| nitrogen | 67.0 | 1877 | 67.0 | 1877 |
| oxygen | 14.3 | 457 | 0.0 | 0 |
| carbon monoxide | 0.0 | 0 | 6.7 | 187 |
| carbon dioxide | 0.0 | 0 | 1.2 | 52 |
| water | 0.0 | 0 | 15.7 | 283 |
| methanol | 0.0 | 0 | 3.9 | 124 |
| mass balance |  | 5343 |  | 5343 |

Carbon dioxide can be used instead of nitrogen in order to dilute the methane/oxygen inlet feed stream to the partial oxidation reactor. Product yield of methanol and carbon monoxide are not adversely affected when carbon dioxide is used as a diluent gas in the range of 0–25 vol. %. In the integrated process, it is desirable to use carbon dioxide as a diluent in an amount of up to about 50 vol. %, preferably in the range of 4–10 vol. %.

The product yield of methanol and carbon monoxide are not adversely affected when between 0–10 vol. % carbon monoxide is added to the inlet feed stream to the partial oxidation reactor. In the integrated process, it is desirable to maintain the concentration of carbon monoxide in the process stream in the range of about 1–25 vol. %, preferably in the range 5–10 vol. %.

EXAMPLE 2

A laboratory scale experiment was carried out in which the carbonylation reactor was operated at a pressure of 1000 psig, a temperature of 185° C. and a GHSV of 4000/h. The composition of the inlet feed stream was chosen to be within the desirable range for the integrated process. The fixed bed reactor having an internal diameter of 0.25 inches was packed with about 0.65 g of a 1 wt. % rhodium catalyst supported on activated carbon, and methyl iodide was used to promote the activity of the rhodium catalyst. In this example, the combined acetic acid and methyl acetate production is 8.2 mmol/h. In the integrated process, methyl acetate is typically hydrolyzed to acetic acid and methanol is recycled to the carbonylation reactor. The reactants used and the results obtained are summarized in Table 2.

TABLE 2

|  | Inlet | | Outlet | |
| --- | --- | --- | --- | --- |
|  | mmol/h | mg/h | mmol/h | mg/h |
| methane | 144.7 | 2321 | 144.7 | 2321 |
| nitrogen | 85.8 | 2402 | 85.8 | 2402 |
| oxygen | 0.0 | 0 | 0.0 | 0 |
| carbon monoxide | 26.8 | 751 | 18.6 | 522 |
| carbon dioxide | 10.7 | 472 | 10.7 | 472 |
| hydrogen | 0.0 | 0 | 0.0 | 0.08 |
| water | 2.8 | 50 | 6.2 | 112 |
| methanol | 3.9 | 124 | 0.2 | 7 |
| injected methanol[+] | 8.0 | 255 | | |
| methyl iodide | 0.7 | 102 | 0.7 | 102 |
| dimethyl ether | | | 0.0 | 1 |
| acetic acid | | | 4.8 | 287 |
| methyl acetate | | | 3.4 | 251 |
| mass balance | | 6477 | | 6477 |

[+]denotes additional methanol to that produced in the partial oxidation reactor.

EXAMPLE 3–7

Laboratory scale experiments were carried out to study the carbonylation reaction under various process conditions of, temperature, pressure, catalyst loading, GHSV, and inlet feed composition. The reactants used and the results obtained are summarized in Table 3.

TABLE 3

| Example | 3 | 4 | 5 | 6 | 7 |
| --- | --- | --- | --- | --- | --- |
| pressure, psig | 1000 | 1000 | 750 | 1220 | 1000 |
| temperature, °C. | 150 | 150 | 185 | 185 | 185 |
| GHSV, /h | 2000 | 2000 | 4000 | 4000 | 4000 |
| Rh loading, wt. % | 4.3 | 1.0 | 1.0 | 0.5 | 1 |
| Feed, mmol/h | | | | | |
| methane | 67.0 | 120.6 | 219.8 | 230.5 | 144.7 |
| nitrogen | | | | | 85.8 |
| carbon monoxide | 67.0 | 13.4 | 26.8 | 26.8 | 26.8 |
| carbon dioxide | | | 21.4 | 10.7 | 10.7 |
| water | 1.4 | 1.4 | 2.8 | 2.9 | 2.8 |
| methanol | 6.2 | 6.2 | 12.3 | 12.6 | 12.9 |
| methyl iodide | 0.4 | 0.4 | 0.8 | 0.8 | 0.4 |
| Product, mmol/h | | | | | |
| dimethyl ether | 0.3 | 0.1 | 0.1 | 0.3 | 0.1 |

TABLE 3-continued

| Example | 3 | 4 | 5 | 6 | 7 |
| --- | --- | --- | --- | --- | --- |
| acetic acid | 5.7 | 0.1 | 1.5 | 0.8 | 1.0 |
| methyl acetate | 0.2 | 1.9 | 3.8 | 3.4 | 4.3 |

I claim:

1. An integrated process for converting methane to acetic acid and/or methyl acetate which comprises subjecting a feed mixture consisting of (a) methane gas and (b) gaseous oxygen, air, or a mixture thereof containing less than 10% by volume of carbon monoxide to partial oxidation without the formation of synthesis gas in a reaction zone at elevated temperature and pressure to form a reaction mixture containing methanol, carbon monoxide, carbon dioxide, methane and water vapor, removing at least a portion of the water vapor from the reaction mixture, feeding the remaining partial oxidation reaction mixture together with additional methanol from an external source through a carbonylation reaction zone at elevated temperature and pressure to form a reaction product containing acetic acid and/or methyl acetate and methanol, said additional methanol being added in an amount such that the additional methanol together with the methanol produced by partial oxidation is sufficient to convert substantially all of the carbon monoxide produced by partial oxidation, recycling excess methane and carbon dioxide from the carbonylation reaction zone back to the partial oxidation reaction zone, recycling methanol in the carbonylation reaction product back to the carbonylation reaction zone and recovering acetic acid and/or methyl acetate as product.

2. A process according to claim 1 wherein the partial oxidation reaction mixture fed to the carbonylation reaction zone contains up to 50% by volume of carbon dioxide.

3. A process according to claim 2 wherein the partial oxidation reaction mixture is passed through a scrubber to remove excess carbon dioxide.

4. A process according to claim 2 wherein the partial oxidation reaction mixture fed to the carbonylation reaction zone contains about 1–25% by volume of carbon dioxide.

5. A process according to claim 2 wherein the partial oxidation reaction mixture contains no more than about 2% by volume of hydrogen.

6. A process according to claim 5 wherein the partial oxidation reaction is carried out at a pressure of at least about 750 psi.

7. A process according to claim 6 wherein the pressure is in the range of 1000–1500 psi.

8. A process according to claim 6 wherein the carbonylation reaction is carried out at substantially the same pressure as the partial oxidation reaction.

9. A process according to claim 8 wherein the additional methanol from an external source comprises up to about 50% by weight of the total methanol fed to the carbonylation reaction zone.

10. A process according to claim 9 wherein the carbonylation reaction is carried out under heterogeneous catalysis.

11. A process according to claim 10 wherein the carbonylation catalyst is selected from the group consisting of rhodium, iridium, cobalt and nickel.

12. A process according to claim 11 wherein the catalyst is an iodide promoted rhodium catalyst.

13. A process according to claim 1 wherein methyl acetate in the reaction product is hydrolyzed to acetic acid.

14. A process according to claim 1 wherein the feed mixture to the partial oxidation contains substantially no carbon monoxide.

* * * * *